United States Patent
Cai et al.

(10) Patent No.: US 11,410,309 B2
(45) Date of Patent: Aug. 9, 2022

(54) METHOD, DEVICE, AND COMPUTER PROGRAM PRODUCT FOR DEEP LESION TRACKER FOR MONITORING LESIONS IN FOUR-DIMENSIONAL LONGITUDINAL IMAGING

(71) Applicant: Ping An Technology (Shenzhen) Co., Ltd., Shenzhen (CN)

(72) Inventors: Jinzheng Cai, Bethesda, MD (US); Youbao Tang, Bethesda, MD (US); Ke Yan, Bethesda, MD (US); Adam P Harrison, Bethesda, MD (US); Le Lu, Bethesda, MD (US)

(73) Assignee: PING AN TECHNOLOGY (SHENZHEN) CO., LTD., Shenzhen (CN)

( * ) Notice: Subject to any disclaimer, the term of this patent is extended or adjusted under 35 U.S.C. 154(b) by 0 days.

(21) Appl. No.: 17/213,804

(22) Filed: Mar. 26, 2021

(65) Prior Publication Data
US 2022/0180517 A1     Jun. 9, 2022

Related U.S. Application Data

(60) Provisional application No. 63/120,780, filed on Dec. 3, 2020.

(51) Int. Cl.
*G06T 7/00* (2017.01)
*G06T 3/00* (2006.01)
(Continued)

(52) U.S. Cl.
CPC ........ *G06T 7/0014* (2013.01); *G06T 3/0006* (2013.01); *G06T 5/50* (2013.01);
(Continued)

(58) Field of Classification Search
CPC ....... G06T 7/0014; G06T 3/0006; G06T 5/50; G06T 2207/20076; G06T 2207/20081;
(Continued)

(56) References Cited

U.S. PATENT DOCUMENTS

2020/0258243 A1*  8/2020  Chang .................. A61B 5/107
2021/0049733 A1*  2/2021  Kang ..................... G06T 7/187
(Continued)

OTHER PUBLICATIONS

Zhou, Z., et al., "3D dense connectivity network with atrous convolutional feature pyramid for brain tumor segmentation in magnetic resonance imaging of human heads," Computers in Biology and Medicine, vol. 121, Jun. 2020, 103766.*

*Primary Examiner* — Xuemei G Chen
(74) *Attorney, Agent, or Firm* — Anova Law Group, PLLC

(57) ABSTRACT

The present disclosure provides a computer-implemented method, a device, and a computer program product for deep lesion tracker. The method includes inputting a search image into a first three-dimensional DenseFPN (feature pyramid network) of an image encoder and inputting a template image into a second three-dimensional DenseFPN of the image encoder to extract image features; encoding anatomy signals of the search image and the template image as Gaussian heatmaps, and inputting the Gaussian heatmap of the template image into a first anatomy signal encoders (ASE) and inputting the Gaussian heatmap of the search image into a second ASE to extract anatomy features; inputting the image features and the anatomy features into a fast cross-correlation layer to generate correspondence maps, and computing a probability map according to the correspondence maps; and performing supervised learning or self-supervised learning to predict a lesion center in the search image.

18 Claims, 9 Drawing Sheets

(51) Int. Cl.
 *G06T 5/50* (2006.01)
 *G06V 10/50* (2022.01)
 *G06V 10/44* (2022.01)

(52) U.S. Cl.
 CPC ............ *G06V 10/457* (2022.01); *G06V 10/50* (2022.01); *G06T 2207/20076* (2013.01); *G06T 2207/20081* (2013.01); *G06T 2207/30096* (2013.01); *G06V 2201/032* (2022.01)

(58) Field of Classification Search
 CPC ........ G06T 2207/30096; G06V 10/457; G06V 10/50; G06V 2201/032
 See application file for complete search history.

(56) References Cited

U.S. PATENT DOCUMENTS

| | | | |
|---|---|---|---|
| 2021/0056693 A1* | 2/2021 | Cheng | G06K 9/6259 |
| 2021/0248736 A1* | 8/2021 | Kamen | G06T 7/11 |
| 2021/0279863 A1* | 9/2021 | Jacenków | G06T 5/002 |
| 2021/0358137 A1* | 11/2021 | Lee | G06N 20/00 |
| 2021/0358296 A1* | 11/2021 | Lee | G06K 9/6259 |
| 2022/0044394 A1* | 2/2022 | Harrison | G16H 30/40 |

\* cited by examiner

METHOD, DEVICE, AND COMPUTER PROGRAM PRODUCT FOR DEEP LESION TRACKER FOR MONITORING LESIONS IN FOUR-DIMENSIONAL LONGITUDINAL IMAGING

CROSS-REFERENCE TO RELATED APPLICATION

This application claims the priority of U.S. Provisional Patent Application No. 63/120,780, filed on Dec. 3, 2020, the entire content of which is incorporated herein by reference.

FIELD OF THE DISCLOSURE

The present disclosure generally relates to the field of lesion tracking technology and, more particularly, relates to a method, a device, and a computer program product for deep lesion tracker for monitoring lesions in four-dimensional longitudinal imaging.

BACKGROUND

Monitoring treatment response by identifying and measuring corresponding lesions is critical in radiological workflows. Manually conducting such procedures is labor-intensive, as expert clinicians must review multiple images and go back and forth between these images for comparison, which is usually subject to considerable inter-observer variability. Therefore, computer aided tools may be applied to lower costs, increase turnaround speeds, and improve reliability.

Automatic image-based lesion monitoring may be decomposed into a plurality of sub-procedures: (1) detecting lesions of interest; (2) then tracking instances of the same lesion across different time points; and (3) measuring changes among the identified instances. The first step of detecting lesions of interest may be formulated as object detection. The computer vision field has made progress for detecting lesions of interest. However, medical imaging has its distinct challenges as the data is often in 3D format (e.g., computed tomography (CT)), and required annotations are unavailable. Therefore, efforts have been made to improve object detection with medical images. Similarly, step (3) also has various viable solutions because it can be formulated as (3D) object segmentation, which is a fundamental topic that attracts attentions from both computer vision and medical image analysis. In contrast, step (2), tracking the same lesion across different time points is not as well developed as lesion detection and segmentation. Part of the lack of development may be attributed to the lack of desirable benchmark datasets to evaluate tracking performance.

Similar with visual tracking in the general computer vision, lesion tracking may be viewed as to match instances of the same lesion in neighboring time frames. However, it is challenging due to changes in size and appearance. Lesion size may enlarge multiple times than its baseline or nadir. Meanwhile, lesion appearance may vary during the follow-up exam because of morphological or functional changes, commonly attributed to necrosis or changes in vascularity. Therefore, an effective tracker should handle both size and visual changes of lesions. Trackers based on image registration are robust to appearance changes, as registration inherently introduces anatomical constraints for lesion matching. The involved body part and surrounding organs of the target lesion are constrained among different images. However, registration methods are usually less sensitive to local image changes; thus, such methods may be inaccurate to track small-sized lesions or lesions with large shape changes. On the other hand, appearance-based trackers handle size and appearance changes by projecting lesion images into an embedding space, where images of the same lesion have similar embeddings and images of different lesions are different from one another. However, the above-mentioned appearance-based trackers may mismatch lesions with visually similar but spurious backgrounds. Therefore, there is a need to design a tracker to conduct appearance based recognition under anatomical constraints by combining the merits of both above-mentioned strategies.

BRIEF SUMMARY OF THE DISCLOSURE

One aspect or embodiment of the present disclosure provides a deep lesion tracker method for medical images. The method includes providing an image pair including a search image and a template image; inputting the search image into a first three-dimensional DenseFPN (feature pyramid network) of an image encoder and inputting the template image into a second three-dimensional DenseFPN of the image encoder to extract image features of the search image and the template image in three different scales, where the first and second three-dimensional DenseFPNs are configured with shared weights; encoding anatomy signals of the search image and the template image as Gaussian heatmaps centered at lesion locations, and inputting the Gaussian heatmap of the template image into a first anatomy signal encoders (ASE) and inputting the Gaussian heatmap of the search image into a second ASE to extract anatomy features of the search image and the template image in three different scales, where the first and the second ASEs are configured with shared weights; inputting the image features and the anatomy features into a fast cross-correlation layer to generate correspondence maps, and computing a probability map according to the correspondence maps; and performing supervised learning or self-supervised learning to predict a lesion center in the search image.

Optionally, encoding the anatomy signals as the Gaussian heatmaps includes: for the template image, using a location and a size of a template lesion to compute the anatomy signals of the template image; and for the search image, using an affine-projected location and an affine-projected size of the template lesion to compute the anatomy signals of the search image.

Optionally, inputting the image features and the anatomy features into the fast cross-correlation layer to generate the correspondence maps includes fusing the image features of the template image and the anatomy features of the template image.

Optionally, after fusing the image features of the template image and the anatomy features of the template image, the method further includes defining a cropping function to extract a template kernel K and another template kernel $K_g$, where a size of the template kernel $K_g$ is greater than a size of the template kernel K; and the template kernel $K_g$ is decomposed into kernels $K_{g,x}$, $K_{g,y}$ and $K_{g,z}$.

Optionally, a correspondence map is computed by:

$$M = (K * S) + \left( \sum_{i \in x,y,z} K_{g,i} * S \right)$$

where + denotes element-wise sum, $S=\psi(I_s)\odot\phi(G_s)$, $I_s$ is the search image, $G_s$ is an anatomy signal map of the search image, $\odot$ denotes element-wise multiplication, and $\psi$ and $\phi$ denote network encoders that generate image features and anatomy features, respectively.

Optionally, after computing the correspondence map, the method further includes determining the lesion center in the search image according to the probability map computed based on the correspondence maps.

Another aspect or embodiment of the present disclosure provides a deep lesion tracker device. The device includes a memory, containing a computer program stored thereon; and a processor, coupled with the memory and configured, when the computer program being executed, to perform a method including: providing an image pair including a search image and a template image; inputting the search image into a first three-dimensional DenseFPN (feature pyramid network) of an image encoder and inputting the template image into a second three-dimensional DenseFPN of the image encoder to extract image features of the search image and the template image in three different scales, where the first and second three-dimensional DenseFPNs are configured with shared weights; encoding anatomy signals of the search image and the template image as Gaussian heatmaps centered at lesion locations, and inputting the Gaussian heatmap of the template image into a first anatomy signal encoders (ASE) and inputting the Gaussian heatmap of the search image into a second ASE to extract anatomy features of the search image and the template image in three different scales, where the first and the second ASEs are configured with shared weights; inputting the image features and the anatomy features into a fast cross-correlation layer to generate correspondence maps, and computing a probability map according to the correspondence maps; and performing supervised learning or self-supervised learning to predict a lesion center in the search image.

Optionally, encoding the anatomy signals as the Gaussian heatmaps includes: for the template image, using a location and a size of a template lesion to compute the anatomy signals of the template image; and for the search image, using an affine-projected location and an affine-projected size of the template lesion to compute the anatomy signals of the search image.

Optionally, inputting the image features and the anatomy features into the fast cross-correlation layer to generate the correspondence maps includes fusing the image features of the template image and the anatomy features of the template image.

Optionally, after fusing the image features of the template image and the anatomy features of the template image, the method further includes defining a cropping function to extract a template kernel K and another template kernel $K_g$, where a size of the template kernel $K_g$ is greater than a size of the template kernel K; and the template kernel $K_g$ is decomposed into kernels $K_{g,x}$, $K_{g,y}$ and $K_{g,z}$.

Optionally, a correspondence map is computed by:

$$M = (K*S) + \left(\sum_{i\in x,y,z} K_{g,i}*S\right)$$

where + denotes element-wise sum, $S=\psi(I_s)\odot\phi(G_s)$, $I_s$ is the search image, $G_s$ is an anatomy signal map of the search image, $\odot$ denotes element-wise multiplication, and $\psi$ and $\phi$ denote network encoders that generate image features and anatomy features, respectively.

Optionally, after computing the correspondence map, the method further includes determining the lesion center in the search image according to the probability map computed based on the correspondence maps.

Another aspect or embodiment of the present disclosure provides a computer program product including a non-transitory computer-readable storage medium and program instructions stored therein, the program instructions being configured to be executable by a computer to cause the computer to implement operations including: providing an image pair including a search image and a template image; inputting the search image into a first three-dimensional DenseFPN (feature pyramid network) of an image encoder and inputting the template image into a second three-dimensional DenseFPN of the image encoder to extract image features of the search image and the template image in three different scales, where the first and second three-dimensional DenseFPNs are configured with shared weights; encoding anatomy signals of the search image and the template image as Gaussian heatmaps centered at lesion locations, and inputting the Gaussian heatmap of the template image into a first anatomy signal encoders (ASE) and inputting the Gaussian heatmap of the search image into a second ASE to extract anatomy features of the search image and the template image in three different scales, where the first and the second ASEs are configured with shared weights; inputting the image features and the anatomy features into a fast cross-correlation layer to generate correspondence maps, and computing a probability map according to the correspondence maps; and performing supervised learning or self-supervised learning to predict a lesion center in the search image.

Other aspects or embodiments of the present disclosure can be understood by those skilled in the art in light of the description, the claims, and the drawings of the present disclosure.

BRIEF DESCRIPTION OF THE DRAWINGS

The following drawings are merely examples for illustrative purposes according to various disclosed embodiments and are not intended to limit the scope of the present disclosure.

DETAILED DESCRIPTION

Figure 1:
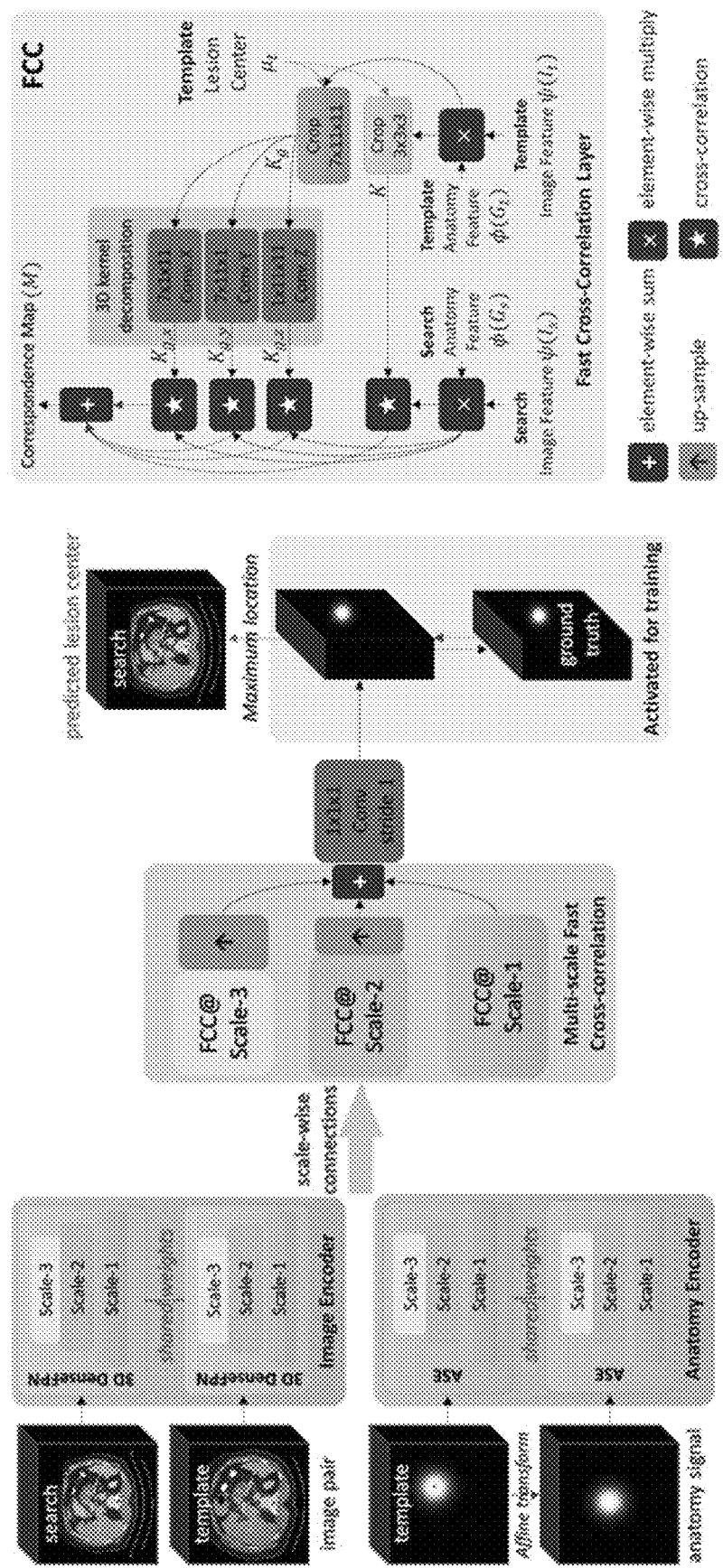
FIG. 1 illustrates an exemplary configuration diagram of deep lesion tracker (DLT) according to various disclosed embodiments of the present disclosure.

Reference may be made in detail to exemplary embodiments of the disclosure, which are illustrated in the accompanying drawings. Wherever possible, the same reference numbers may be used throughout the drawings to refer to the same or like parts.

While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be interpreted as open ended, such that an item or items following any one of these words is not meant to be an exhaustive listing of the item or items, or meant to be limited to only the listed item or items. And the singular forms "a," "an," and "the" are intended to include plural references, unless the context clearly dictates otherwise.

For tracking as similarity learning, tracking of target objects may be achieved via similarity comparisons between an object template and proposals from a search domain. Similarities may be measured by either color/intensity representations, spatial configurations, or combinations thereof. Deep learning features may be more widely used for visual tracking as they outperform hand-crafted features with more expressive representations. To efficiently extract and compare deep learning features, SiamFC and CFNet may use a cross-correlation layer at the end of Siamese architectures. The cross-correlation layer may use Siamese feature maps extracted from a template image patch as a kernel to operate fully circular convolution on the corresponding Siamese feature maps of a search image. The above-mentioned procedure may encode the information regarding the relative position of the target object inside the search image. Within the same framework of SiamFC, SiamRPN++ may introduce strategies to allow training of Siamese networks with modern very deep networks, for example, dense convolutional network (DenseNet), to further boost tracking accuracy. This is critical for medical image analysis as various medical applications lack large-scale training data and rely on transfer learning of pre-trained networks for desirable performance. Siamese networks have also been applied in medical image analysis. For example, 2D Siamese networks may be applied to track liver landmarks in ultra-sound videos; similar 2D Siamese networks may be extended in a coarse-to-fine fashion; while, 3D Siamese networks with computed tomography (CT) series may be performed, only shallow network architectures may be evaluated on tracking lung nodules. In contrast, the present disclosure may follow SiamRPN++ to use Siamese networks with 3D DenseNet backbones which is applied to conduct universal lesion tracking in whole body CT images. Processing different types of lesions with a unified deep learning model may demonstrate computational efficiency and alleviate model overfitting. Different from prior formulations of Siamese networks, a simple but effective 3D kernel decomposition may be configured to speed up 3D cross-correlation operations for object matching, which may provide significant boosts in efficiency, reducing over 65% of FLOPs (floating point operation) in a fast cross-correlation (FCC) layer.

For tracking as detector learning, tracking as detector learning may rely on developing discriminative models to separate a target from background regions. A discriminative model that is suitable for visual tracking may include two core components, namely a classifier that can be efficiently updated online during visual tracking and a feature representation, for example, features extracted by convolutional neural networks (CNNs) that can let the classifier easily differentiate objects in the feature space. Following the above-mentioned strategy, SO-DLT (structured output deep learning tracker), FCNT (fully convolutional network based tracker), and MDNet (multi-domain network) may all train CNNs offline from large-scale object recognition tasks so that the learnt feature representation is general with visual objects. During the tracking process, the lower layers of the network may be frozen as a feature extractor and the higher layers of the network may be updated to adapt to a specific video domain. The tracking strategy via detector learning may be considered, and accordingly strong lesion tracking baselines may be constructed. Given the specialty of processing medical data, especially 4D CT images (3D image plus time), there are no baseline methods ready for comparison. Thus, own lesion tracking baselines may be constructed by concatenating existing lesion detection models with deep learning feature extractors. However, the tracker developed with such strategy may be sub-optimal since the feature extractors of detection models are developed from independent offline tasks. The feature extractors of detection models may convert the object template and proposals from a search domain into a template feature representation and certain proposal feature representations, respectively. The proposal feature representations may then be compared with the template feature representation one after another and the proposal with the most similar proposal feature representation with the template feature representation may be selected as the tracked lesion. In contrast, the present disclosure may use DLT to unify the tasks of feature extraction and target object localization in an end-to-end structure, which may outperform above-mentioned detector learning baselines, thereby implementing higher accuracy and faster speed.

For tracking priors from image registration, visual tracking in video may follow a prior of spatial consistency, which indicates the search space in the next video frame can be constrained to be near to the current location. Such prior may be helpful for improving tracking efficiency and making the model robust to background distractors. Similarly, lesion tracking in CT should follow a spatial consistency governed by anatomical considerations, which implies that the surrounding organs and structures of a lesion may not drastically change. Under such constraints, image registration approaches may perform lesion tracking via image alignment. For example, registration approaches may be used to optimize the global structural alignment, including accurately align boundaries of large organs, while being robust to local changes. Nonetheless, although reported results may suggest that registration approaches are useful for aligning large-sized lesions, such approaches may fail to track small-sized lesions and struggle whenever there are local changes in the lesion's appearance. In contrast, the present disclosure may improve the capabilities of registration approaches using deep learning based lesion appearance recognition to match lesions based on both visual and anatomical signals. For example, the location of a target lesion may be first roughly initialized using image registration, such as affine registration; then, a DLT deep learning model may refine the location to the lesion center using appearance-based cues. In contrast with approaches that use the spatial and structural priors simply in pre- or post-processing, the DLT may takes the priors as its inputs and propagate the priors together with CT-based visual signal to generate the final target location. The priors may also function as attention guidance, letting the appearance learning focus on vital image regions.

Various embodiments provide a method, a device, and a computer program product for DLT. The DLT is described in detail according to various embodiments of the present disclosure hereinafter.

FIG. 1 illustrates an exemplary DLT configuration diagram according to various disclosed embodiments of the present disclosure. The DLT may be based on the structure of Siamese networks because such networks are efficient and deliver promising visual tracking performance for various computer vision tasks. The core component of Siamese-based tracking may be a correlation filter which is also known as a cross-correlation layer. Siamese features extracted from a template image patch may be used as a kernel to perform explicit convolutional scanning over the entire extent of feature maps of a search image. The DLT may be applied to process three dimensional medical data (e.g., CT images). Therefore, network backbones in 3D may be created and an anatomy signal encoder (ASE) may be introduced to guide lesion tracking with anatomical constraints. To avoid the prohibitive computational expenses of 3D cross-correlation between the template image and the search image, a simple and effective formulation may be used to speed up the procedure in the present disclosure. $I_t$ and $I_s$ are used to respectively denote a template and a search CT image. In $I_t$, a lesion is known with its center $\mu_t$ and radius $r_t$. Given $I_t$, $I_s$, $\mu_t$, and $r_t$, the task of lesion tracking is to locate the same lesion in $I_s$ by predicting its new center $\mu_s$.

Figure 2:
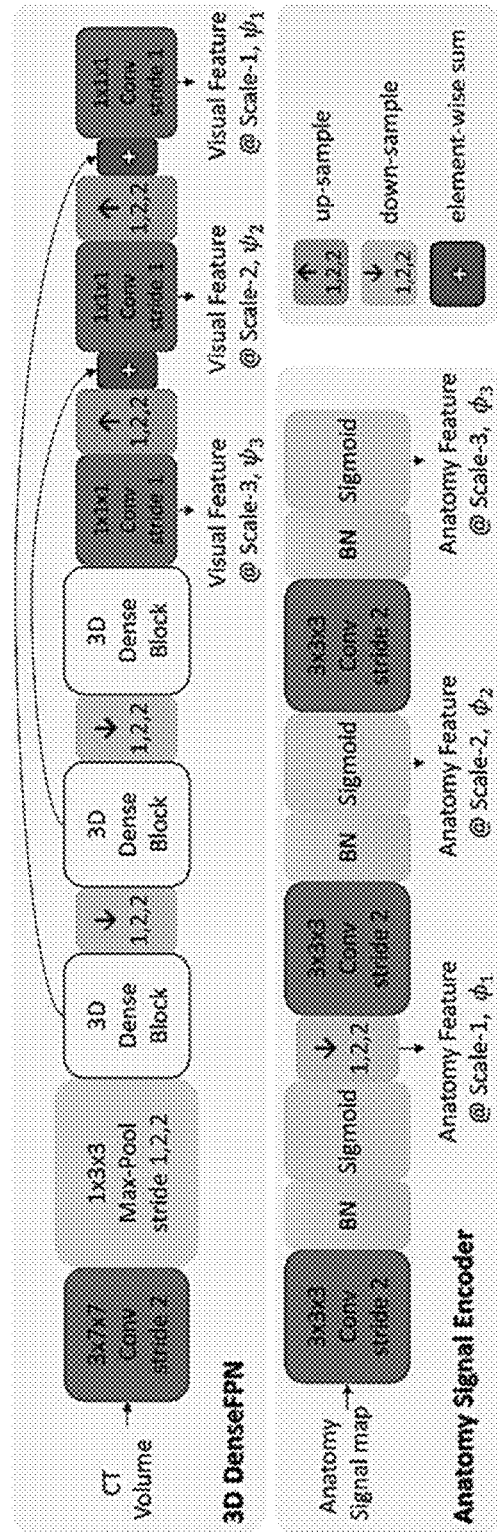
FIG. 2 illustrates an exemplary network configuration diagram of an image encoder 3D DenseFPN (feature pyramid network) and an anatomy signal encoder (ASE) according to various disclosed embodiments of the present disclosure.

In lesion tracking, the Siamese network needs to process lesions with varied appearances and sizes in 3D images. FIG. 2 illustrates an exemplary network configuration diagram of an image encoder 3D DenseFPN (feature pyramid network) and an anatomy signal encoder (ASE) according to various disclosed embodiments of the present disclosure. As shown in FIG. 2, a deep 3D image encoder with large model capacity may be configured in the present disclosure, such that effective feature representations may be learned. For example, DenseNet may be transformed into 3D by duplicating its 2D convolutional kernels along the third direction and then downscaling weight values by the number of duplications. Such configuration may be found to be more effective than 3D UNet on modeling universal lesion appearances. A FPN may be then added after the 3D DenseNet to generate visual (e.g., image) features in three different scales. For clarity, $\psi_1$, $\psi_2$, and $\psi_3$ may refer to the image mapping functions (e.g., the image network encoder) that generate (image) feature maps from the largest to the smallest resolutions, respectively.

It can be noted that directly implementing lesion tracking with Siamese networks may produce matches with visually similar but spurious regions. In contrast, affine registration is a robust approach to roughly align CT images, which is achieved by solving the following equation:

$$\mathcal{T}_{Aff} = \underset{\mathcal{T}_{Aff} \in \mathcal{A}}{\arg\min} \|\mathcal{T}_{Aff}(I_t) - I_s\|_1 \tag{1}$$

where $\mathcal{A}$ is the space of affine transforms. The projected location of the template lesion, $\mathcal{T}_{Aff}(\mu_t)$, may be located close to the actual target lesion. While affine registration has been used as pre-processing or post-processing in the existing technology, affine registration may not provide mechanisms for incorporation into a tracking pipeline that cross-correlates template features across the entire extent of the search image. For example, pre-registering may have minimal effect on the translation-invariant cross-correlation. Instead, as shown in FIG. 1, anatomy signals may be encoded as Gaussian heatmaps centered at lesion locations using the following equation:

$$\mathcal{G}(\mu, nr) = \exp\left(-\frac{\sum_{i \in \{x,y,z\}} (i - u^i)^2}{2(nr)^2}\right) \tag{2}$$

where n=4 is found to deliver the desirable performance. For $I_t$, the template lesion location and size may be used to calculate $\mathcal{G}(\mu_t, nr_t)$. For $I_s$, the affine-projected location and size of the template lesion may be used to calculate $\mathcal{G}(\mathcal{T}_{Aff}(\mu_t), n\mathcal{T}_{Aff}(r_t))$. For clarity, the template and search anatomy signal maps are refer as $G_t$ and $G_s$, respectively; and SimpleElastix is used to solve equation (1).

In various embodiments of the present disclosure, the network configuration of the ASE is shown in FIG. 2. ASE may encode anatomical signals into high-dimensional anatomical features with three different resolutions. In correspondence with 3D DenseFPN, the network functions for the three scales may be denoted as $\phi_1$, $\phi_2$ and $\phi_3$ from the largest to the smallest, respectively, which may be generated by the anatomy network encoder.

As mentioned above, correlation is a core operation of Siamese-based tracking, which creates a correspondence map between target and search features, $\psi(I_t)$ and $\psi(G_t)$, respectively. Because the same operation is performed at each scale, the scale subscripts are dropped herein for simplicity. To conduct cross-correlation, image and anatomy features may be fused first. For example, to fuse $\psi(I_t)$ and $\phi(G_t)$, the following equation is used:

$$F = \psi(I_t) \odot \phi(G_t) \tag{3}$$

where $\odot$ is element-wise multiplication, and $\phi(G_t)$ may be constrained to have the same shape as $\psi(I_t)$. It may be noted that fusing $\psi(I_t)$ and $\phi(G_t)$ with $\odot$ may perform better than channel-wise concatenation. Next, a cropping function to extract a 3×3×3 template kernel may be defined as:

$$K = \mathcal{C}(F, \mu_t, (3,3,3)) \tag{4}$$

where the kernel is centered at $\mu_t$ after potential feature downscaling. To encode the global image context better, another larger size kernel $K_g = \mathcal{C}(F, \mu_t, (7,11,11))$ may also be extracted. The size along the z-direction may be limited to be 7 since the size of $I_t$ during model training is only (32, 384, 384).

Following an existing cross-correlation operation, the correspondence map is defined as:

$$M = (K * S) + (K_g * S) \tag{5}$$

where $S = \psi(I_s) \odot \phi(G_s)$, and + is the element-wise sum. A direct use of $K_g$ may introduce a heavy computational load. Therefore, $K_g$ may be decomposed along the axial, coronal, and sagittal directions, and flattened kernels may be obtained as $K_{g,z} \in \mathcal{R}^{(1,11,11)}$, $K_{g,x} \in \mathcal{R}^{(7,1,11)}$ and $K_{g,y} \in \mathcal{R}^{(7,11,1)}$ may be obtained, where batch size dimensions may be omitted for clarity. As shown in FIG. 1, the FCC layer may perform the flattening using learned 3D convolutions configured to produce an output of identical size as the kernel, except with one dimension flattened. The resulting faster version of equation (5) is:

$$M = (K*S) + \left(\sum_{i \in x,y,z} K_{g,i} * S\right) \quad (6)$$

Kernel decomposition may also be tested by simply extracting the middle "slices" of $K_9$ along the three dimensions, but such decomposition may not perform as well as the learned flattening operations.

Adding back the scale subscripts, the final output is a probability map:

$$\hat{Y} = \sigma(W^T(M_1 + U_2 + U_3) + b) \quad (7)$$

where $\sigma(\cdot)$ is the Sigmoid function, W and b are parameters of the final fully convolutional layer, $U_2$ is $M_2$ up-scaled by (1, 2, 2), and $U_3$ is $M_3$ up-scaled by (1, 4, 4). The predicted lesion center $p_p$ is the index of the global maximum in $\hat{Y}$. The probability map may the same size with the search image. Each pixel of the probability map may have a probability value that indicates what the probability of the corresponding pixel in the search image is to be the center of the target lesion. The position with the maximum probability value in the probability map may be used as the tracked center of the target lesion.

The DLT is capable of both supervised and self-supervised learning (SSL), which is flexible to learn from paired annotations and to use efficient self-supervised learning.

For supervised training in various embodiments of the present disclosure, based on the above-mentioned network architecture, the output of the DLT ($\hat{Y}$) is a dense probability map representing the likelihood of each location to be the target lesion center. Therefore, the ground truth may be defined as a Gaussian kernel centered at the target location $\mu_t$. Formally, $Y = \mathcal{G}(\mu_s, r_s)$ may be first defined and then downsized to match the dimensions of $\hat{Y}$. Focal loss may be used in training as the following:

$$\mathcal{L}_{sl} = \sum_i \begin{cases} (1-\hat{y}_i)^\alpha \log(\hat{y}_i) & \text{if } y_i = 1 \\ (1-y_i)^\beta (\hat{y}_i)^\alpha \log(1-\hat{y}_i) & \text{otherwise} \end{cases} \quad (8)$$

where $y_i$ and $\hat{y}_i$ are the i-th voxels in Y and $\hat{Y}$, respectively, and $\alpha=2$ and $\beta=4$ are focal-loss hyper-parameters. The ground-truth heat map is <1 everywhere except at the lesion center voxel, such that the training may converge quickly and ignore hard voxels that are near $\mu_s$.

For center augmentation in various embodiments of the present disclosure, practically, labels from clinicians may not represent the exact lesion centers, and provided location $\mu_t$ may shift inside the central area; therefore, to increase model robustness, the DLT may be trained with random location shifts, which is achieved by adding $\mu_t$ with $\Delta\mu_t$, which is randomly sampled from the sphere $\|\Delta\mu_t\|_2 \leq 0.25\ r_t$.

For self-supervised training in various embodiments of the present disclosure, since the DLT is built upon Siamese pair-wise comparison, the DLT inherently supports learning with self-supervision. The key insight is that effective visual representation for object recognition may be learned by comparing the template image $I_t$ with its augmented counterparts. With $I_t$, data augmentations may include (1) elastic deformations at random scales ranging from 0 to 0.25, (2) rotations in the xy-plane with a random angle ranging from −10 to 10 degrees, (3) random scales ranging from 0.75 to 1.25, (4) random crops, (5) adding Gaussian noise with zero mean and a random variance ranging from 0 to 0.05, and (6) Gaussian blurring with a random sigma ranging from 0.5 to 1.5. Each augmentation may individually take place with the probability of 0.5. For clarity, $\mathcal{T}_{aug}$ may be defined as any combination of the data augmentations. Therefore, each self-supervised image "pair" may comprise $I_t$ and $\mathcal{T}_{aug}(I_t)$ with corresponding anatomical signals of comprise $G_t$ and $\mathcal{T}_{aug}(G_t)$. A same training procedure as supervised learning may then be followed. It should be noted that the above-mentioned SSL strategy may share a similar spirit with other corresponding contrastive learning studies that matches an image with its transformed version, but in the pixel-level.

In various embodiments of the present disclosure, non-longitudinal images may be selected from DeepLesion and the bounding box annotations may be used as $\mu_t$ and $r_t$. When bounding box annotations are not available, the template lesions may be extracted by applying a pre-trained universal lesion detector on $I_t$ and randomly selecting top-scoring proposals.

Limited by GPU memory, when combining the supervised learning with SSL, the training of the DLT may be switched between both schemes as:

$$\mathcal{L}_{mix} = \begin{cases} \mathcal{L}_{ssl} & \text{if } \lambda \leq \tau \\ \mathcal{L}_{sl} & \text{otherwise} \end{cases} \quad (9)$$

where $\lambda \in [0,1]$ is a random number, and a threshold i is empirically to set as 0.25 in various embodiments of the present disclosure.

Figure 3:
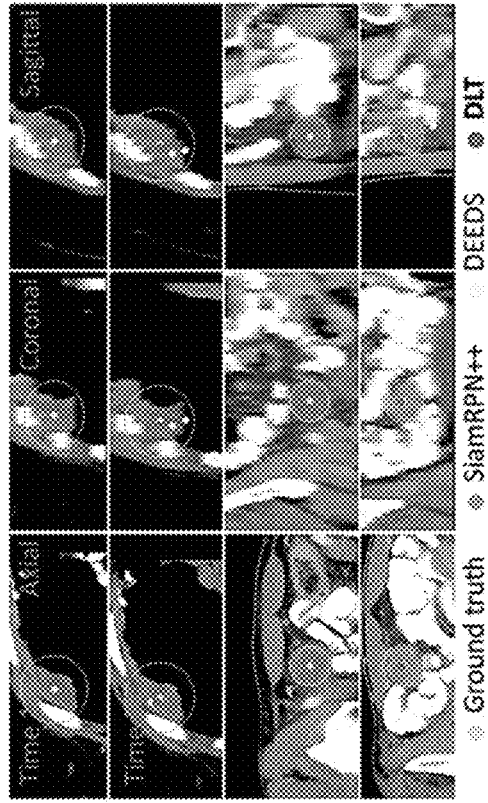
FIG. 3 illustrates an exemplary schematic of 3D tracking comparisons according to various disclosed embodiments of the present disclosure.

In various embodiments of the present disclosure, introducing the public benchmark and also formulating the lesion tracking solution (called the DLT) may both be used. The DLT may accurately match instances of the same lesion across different images captured at different time points and contrast phases by using both appearance and anatomical signals. FIG. 3 illustrates an exemplary schematic of 3D tracking comparisons according to various disclosed embodiments of the present disclosure. Referring to FIG. 3, the comparison of the existing lesion tracking approaches and the DLT may be illustrated.

Figure 4:
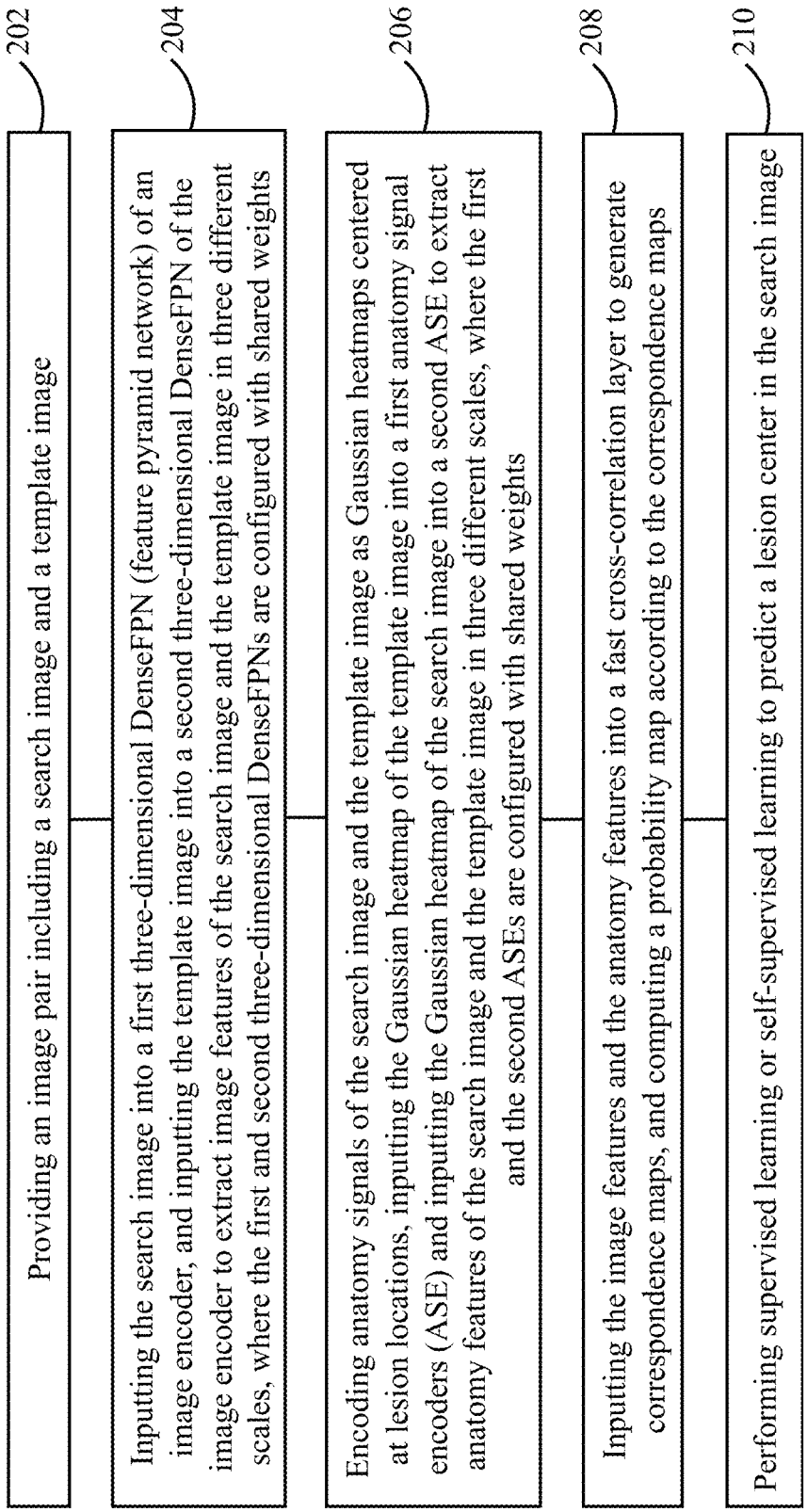
FIG. 4 illustrates a flow chart illustrating an exemplary training process of deep lesion tracker (DLT) according to various disclosed embodiments of the present disclosure.

FIG. 4 illustrates a flow chart illustrating an exemplary training process of the DLT according to various disclosed embodiments of the present disclosure.

At S202, an image pair including a search image and a template image may be inputted.

At S204, the search image may be inputted into a first three-dimensional DenseFPN (feature pyramid network) of an image encoder and the template image may be inputted into a second three-dimensional DenseFPN of the image encoder to extract image features (e.g., feature maps) of the search image and the template image in three different scales, where the first and second three-dimensional DenseFPNs are configured with shared weights;

At S206, anatomy signals of the search image and the template image may be encoded as Gaussian heatmaps centered at lesion locations, and the Gaussian heatmap of the template image may be inputted into a first anatomy signal encoders (ASE) and the Gaussian heatmap of the search image may be inputted into a second ASE to extract anatomy features of the search image and the template image in three different scales, where the first and the second ASEs are configured with shared weights;

At S208, the image features and the anatomy features may be inputted into a fast cross-correlation layer to generate correspondence maps, and a probability map may be computed according to the correspondence maps.

At S210, supervised learning or self-supervised learning may be performed to predict a lesion center in the search image.

DeepLesion is a large-scale CT database of lesions released by the National Institute of Health (NIH) in 2018 which contains over 30 thousand lesions; and each lesion is associated with a size measurement defined by the response evaluation criteria in solid tumors (RECIST). The RECIST measurement includes two diameters: the longest diameter followed by the longest diameter that is perpendicular to the first longest diameter; and both diameters are drawn by doctors in a manually selected axial slice. The RECIST measurement is a cross mark including two perpendicular line segments. The first line segment may be the longest diameter of the target tumor/lesion. The second line segment, which is in the direction that is perpendicular to the first line segment, may be the longest diameter of the target tumor/lesion in such direction. Based on such measurement, the ground truth lesion center $\mu$ is defined to be the mean of diameters' four end points, and the radius r is approximated to be the half of the longest diameter. In total, the publicly released deep longitudinal study (DLS) dataset inherits about 3008, 403, and 480 lesion pairs from the DeepLesion's training, validation, and testing splits, respectively.

In one embodiment of the present disclosure, from a collaborated anonymous hospital, an external validation set that includes 536 lesions from 100 longitudinal studies may also be collected. A desirable DLT configuration, developed on the DeepLesion dataset, may be applied to track the corresponding existing target lesions. To assess the tracking accuracy, the acceptance rate of an board-certificated radiologist with over 10 years of clinical practice experience may be measured.

Evaluation metrics may be described in various embodiment of the present disclosure. For an annotated pair of lesion a and b, tracking both from a to b and from b to a may be evaluated. Therefore, in total, 906 and 960 directed lesion pairs may be in the validation and test sets, respectively. A center point matching (CPM) accuracy, which represents the percentage of correctly matched lesions, may be defined. A match may be counted correct when the Euclidean distance between the ground truth center and the predicted center is smaller than a threshold. The threshold may be set to be the corresponding lesion radius and refer to the matching accuracy CPM@Radius or simply CPM. However, the threshold may not be tight enough to differentiate trackers as certain lesions have large sizes. Then, an adaptive threshold min (r, 10 mm) may be used to limit the allowed maximum offset in large lesions, and such matching accuracy may be referred as CPM@10 mm. The absolute offset between ground truth and predicted centers in mm may also be measured and the mean Euclidean distance (MED) and corresponding projections $MED_x$, $MED_y$, $MED_z$ in each direction may be reported. The speed of trackers may be counted using seconds per volume (spv).

In one embodiment of the present disclosure, for existing registration approaches, both the widely used rigid affine registration method and DEEDS (DEnsE Displacement Sampling) deformable registration may be used. The applied implementation may be optimized in C++, and the CT volumes may have been resampled to the isotropic resolution of 2 mm.

In one embodiment of the present disclosure, for learning based registration approaches, VoxelMorph, which is a general deep learning framework for deformable medical image registration that can deliver desirable performance with a significantly faster speeds than existing approaches, may be used. VoxelMorph may be trained with image pairs from DLS. Image pairs may be first aligned by affine registration and then resampled to 0.8 mm by 0.8 mm in x, y-plane with a slice thickness of 2 mm. A same image resolution may be applied according to various embodiments of the present disclosure.

In one embodiment of the present disclosure, for tracking by detector learning, lesion candidates may be first detected; an image encoder may then be used to project both the template lesion and the detected candidates into feature vectors; and lastly, a nearest neighbor classifier may be applied to identify the tracked lesion. The detector may be tested with the 2D LENS and 3D VULD detectors which have desirable performance on DeepLesion. As for the image encoder, LesionGraph and LesaNet, which are also developed from DeepLesion for lesion attribute description, may be tested. Therefore, four baselines, including LENS-LesionGraph, LENS-LesaNet, VULD-LesionGraph, and VULD-LesaNet, may be evaluated according to various embodiments of the present disclosure.

In one embodiment of the present disclosure, for tracking by similarity learning, SiamRPN++ may be adapted with 3D DenseFPN so that it can process CT images and perform rational comparison with the DLT. The largest size of the template kernel may be (3, 5, 5) for computational efficiency.

In one embodiment of the present disclosure, for the DLT and corresponding variants, the DLT may be trained using the DLS dataset; and DLT-SSL may be trained using only SSL with non-longitudinal training images of DeepLesion that do not exist in DLS. DLT-Mix may be trained with a combination of supervised and self-supervised learning, which is defined by equation (9).

Table 1 illustrates the comparative results between the DLT and other existing tracking approaches. With CPM@10 mm, the DLT and DLT-Mix may achieve the first and second places, respectively, leading DEEDS at the third place by over 6%. The DLT-SSL may be at the fourth place outperforming its SSL counterparts, for example, affine registration and VoxelMorph, by over 20%. With CPM@Radius, the DLT-Mix may be the highest performance tracker since such method outperforms DEEDs and SiamRPN++ by about 3.2% and about 8.4%, respectively. With MED, the DLT may have desirable performance, but LENS-LesionGraph may outperform the DLT in MEDx by a large margin, for example, about 0.9 mm, which is because LENS is a 2D detector with a bounding-box regression layer dedicated to locating the lesion accurately in the x, y-plane. Similarly, LENS-LesaNet may outperform the DLT by about 0.3 mm in MED However, in MEDz, the DLT may outperforms LENS-LesionGraph and LENS-LesaNet by about 2 mm and about 1.7 mm, respectively, showing the importance of 3D DenseFPN. In terms of speed, affine registration and VoxelMorph may be the top 2 methods but they are not as accurate as the other approaches. Among the top 3 methods, the DLT and DLT-Mix may operate about 4 times faster than DEEDS on the DeepLesion dataset.

TABLE 1

Comparisons of the DLT with other existing tracking approaches.

| Method | CPM@ 10 mm | CPM@ Radius | MED$_X$ (mm) | MED$_Y$ (mm) | MED$_Z$ (mm) | MED (mm) | Speed (spv) |
|---|---|---|---|---|---|---|---|
| Affine | 48.33 | 65.21 | 4.1 ± 5.0 | 5.4 ± 5.6 | 7.1 ± 8.3 | 11.2 ± 9.9 | 1.82 |
| VoxelMorph | 49.90 | 65.59 | 4.6 ± 6.7 | 5.2 ± 7.9 | 6.6 ± 6.2 | 10.9 ± 10.9 | 0.46 |
| LENS-LesionGraph | 63.85 | 80.42 | 2.6 ± 4.6 | 2.7 ± 4.5 | 6.0 ± 8.6 | 8.0 ± 10.1 | 4.68 |
| VULD-LesionGraph | 64.69 | 76.56 | 3.5 ± 5.2 | 4.1 ± 5.8 | 6.1 ± 8.8 | 9.3 ± 10.9 | 9.07 |
| VULD-LesaNet | 65.00 | 77.81 | 3.5 ± 5.3 | 4.0 ± 5.7 | 6.0 ± 8.7 | 9.1 ± 10.8 | 9.05 |
| SiamRPN++ | 68.85 | 80.31 | 3.8 ± 4.8 | 3.8 ± 4.8 | 4.8 ± 7.5 | 8.3 ± 9.2 | 2.24 |
| LENS-LesaNet | 70.00 | 84.58 | 2.7 ± 4.8 | 2.6 ± 4.7 | 5.7 ± 8.6 | 7.8 ± 10.3 | 4.66 |
| DLT-SSL | 71.04 | 81.52 | 3.8 ± 5.3 | 3.7 ± 5.5 | 5.4 ± 8.4 | 8.8 ± 10.5 | 3.57 |
| DEEDS | 71.88 | 85.52 | 2.8 ± 3.7 | 3.1 ± 4.1 | 5.0 ± 6.8 | 7.4 ± 8.1 | 15.3 |
| DLT-Mix | 78.65 | 88.75 | 3.1 ± 4.4 | 3.1 ± 4.5 | 4.2 ± 7.6 | 7.1 ± 9.2 | 3.54 |
| DLT | 78.85 | 86.88 | 3.5 ± 5.6 | 2.9 ± 4.9 | 4.0 ± 6.1 | 7.0 ± 8.9 | 3.58 |

Figure 5:
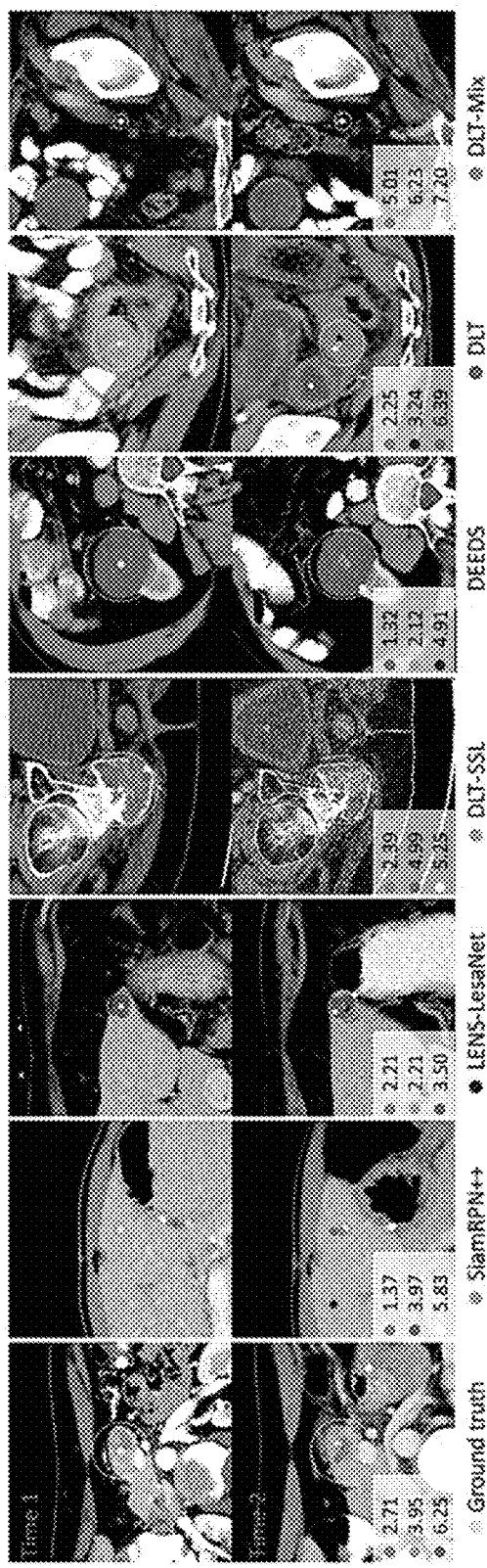
FIG. 5 illustrates an exemplary schematic of method comparisons according to various disclosed embodiments of the present disclosure.
Figure 6:
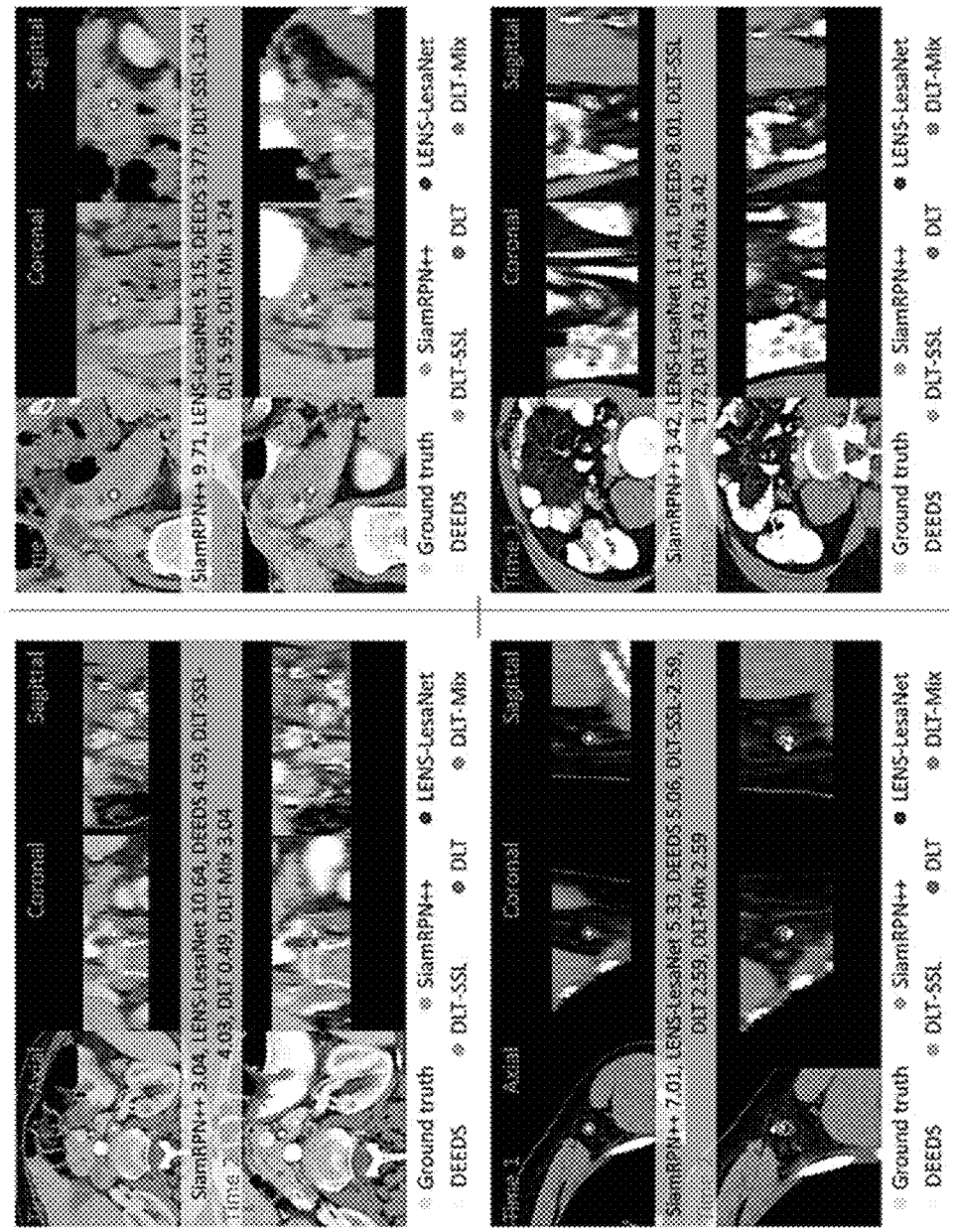
FIG. 6 illustrates another exemplary schematic of method comparisons according to various disclosed embodiments of the present disclosure.
Figure 7:
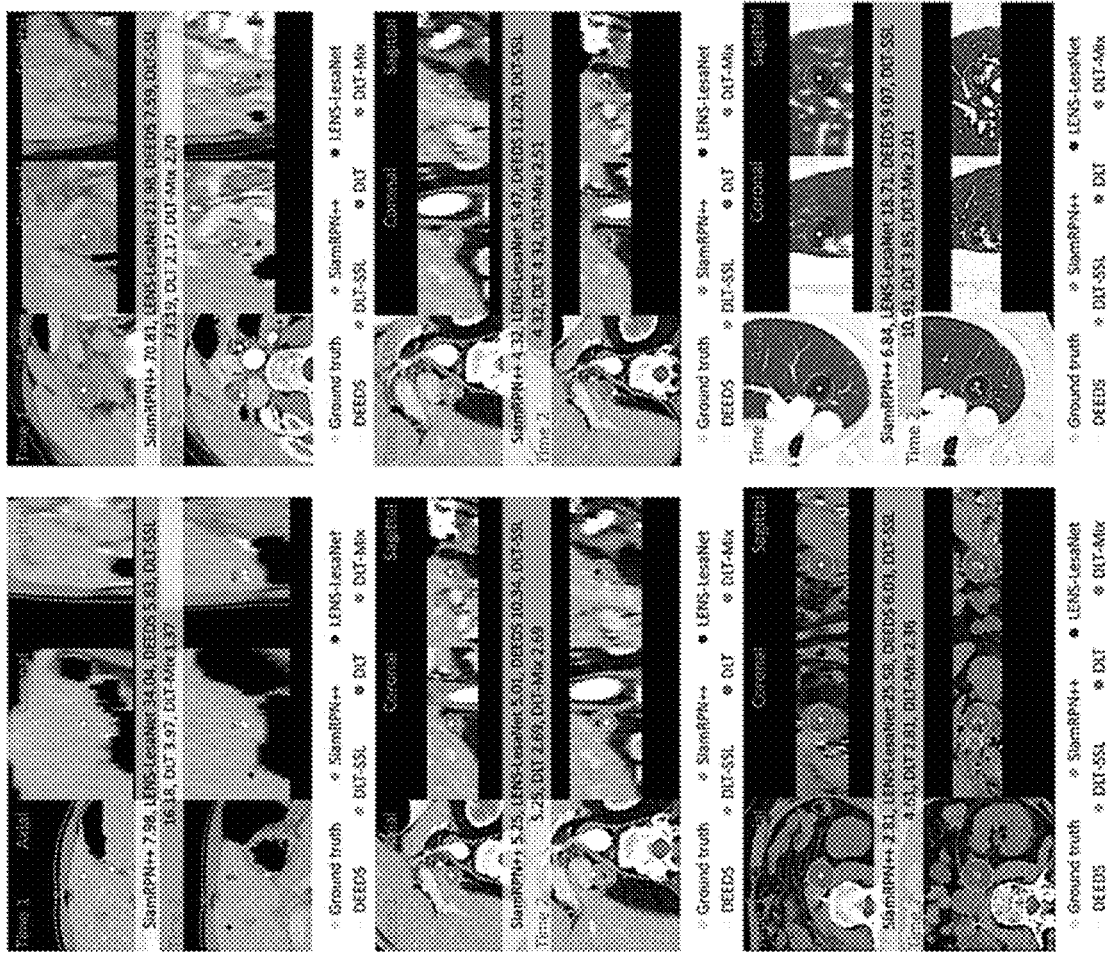
FIG. 7 illustrates another exemplary schematic of method comparisons according to various disclosed embodiments of the present disclosure.
Figure 8:
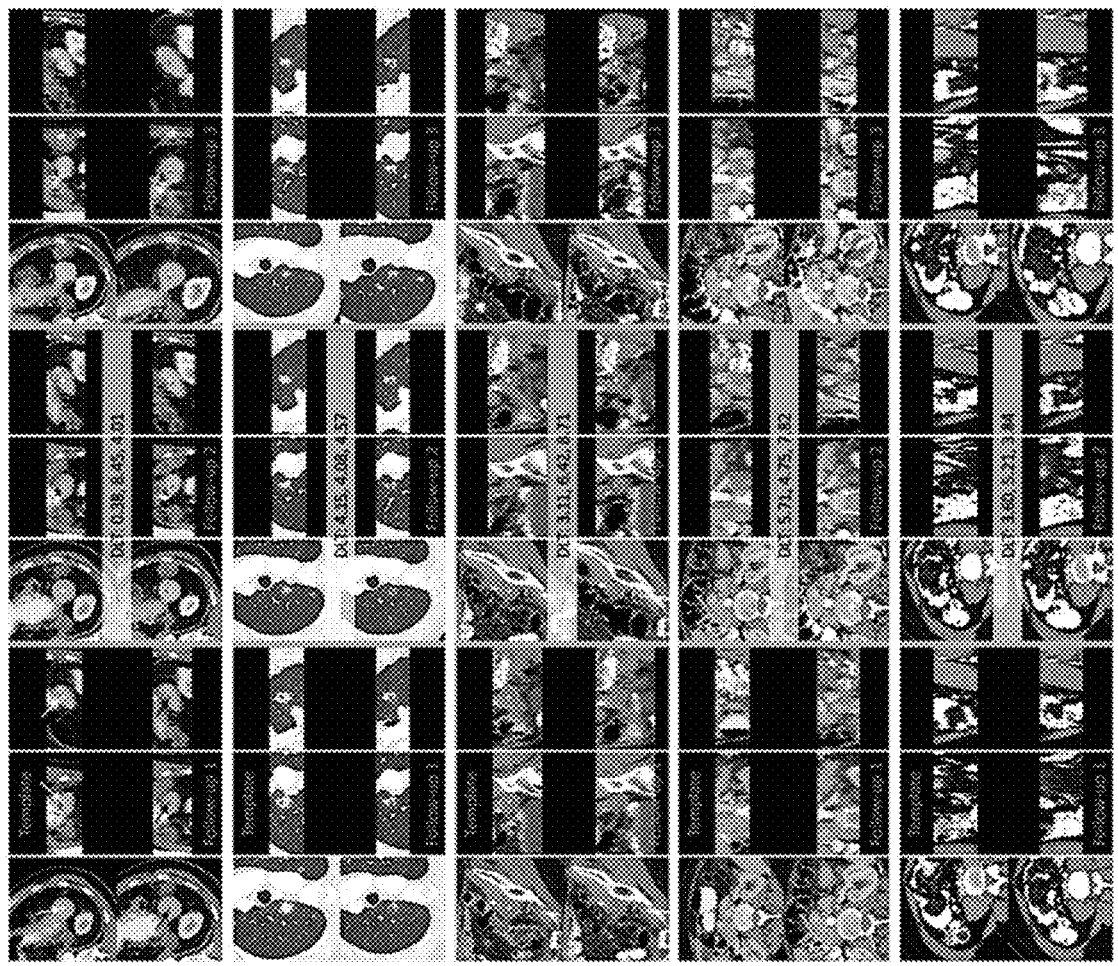
FIG. 8 illustrates an exemplary schematic of lesion tracking using deep lesion tracker (DLT) according to various disclosed embodiments of the present disclosure.
Figure 9:
FIG. 9 illustrates another exemplary schematic of lesion tracking using deep lesion tracker (DLT) according to various disclosed embodiments of the present disclosure.
Figure 10:
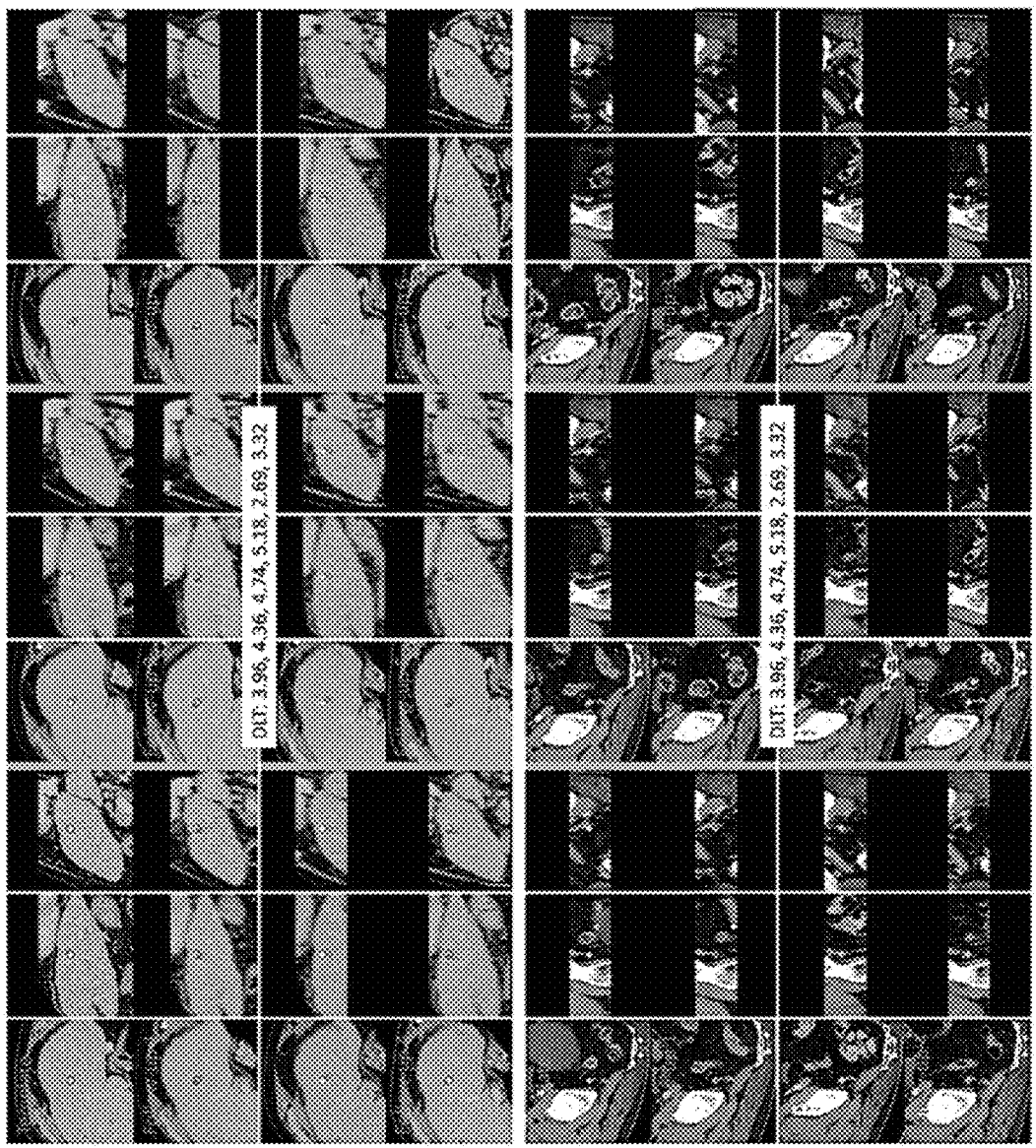
FIG. 10 illustrates another exemplary schematic of lesion tracking using deep lesion tracker (DLT) according to various disclosed embodiments of the present disclosure.

FIGS. 5-7 illustrate exemplary schematics of method comparisons according to various disclosed embodiments of the present disclosure. For example, referring to FIG. 5, seven visual examples of lesion tracking may be illustrated, where the results produced by the DLT trackers are closer to the ground truth than other approaches. Referring to FIGS. 5-7, the methods including DLT, DLT-SSL, DLT-Mix may be compared with three existing trackers including a Siamese networks based tracker (SiamRPN++), a leading registration algorithm (DEEDS), and a detector based tracker (LENS-LesaNet). Offsets from the predicted lesion centers to the manually labeled center may be reported in mm. FIGS. 8-10 illustrates exemplary schematics of lesion tracking using the DLT according to various disclosed embodiments of the present disclosure. For example, referring to FIG. 8, the template image may be sampled from the first exam, and then follow-up 1, 2, and 3 may be sampled from times of the second, third, and fourth exams, respectively. For example, white arrows and black arrows may respectively indicate the manually labeled centers and DLT predicted centers. Only the lesion center and radius at the first time point may be given; and offsets from the DLT predicted lesion center to the manually labeled center may be reported in mm.

In various embodiments of the present disclosure, human inputs may be simulated for robustness evaluation. In testing, the template center $\mu_t$ with $\Delta\mu_t$, which is randomly sampled from the sphere $\|\Delta\mu_t\|_2 \leq 0.25\ r_t$, may be shifted. For each directed lesion pair, 9 shifted centers together with the original center may be stored. In total, about 9060 and 9600 directed lesion pairs may be created from the validation and testing sets, respectively. With such augmented lesion pairs, the DLT trackers may be evaluated to determine whether they are robust with inaccurate human inputs or not.

Table 2 demonstrates the results of robustness evaluation, where ↓ and ↑ demonstrate decrease and increase of measurements, respectively, compared with the values reported in Table 1. The DLT-Mix may be in the first place for both CPM and MED metrics. DEEDS may be the most vulnerable method with over 10% drop in CPM and about 2.4 mm increase in MED. In comparison, the DLT-Mix may only drop about 1.87% in CPM and increases only about 0.9 mm in MED. Additionally, the DLT-SSL may be more robust than the DLT in CPM, demonstrating the benefit of SSL in training robust trackers.

TABLE 2

Robust evaluation of different tracking approaches.

| Method | CPM@ Radius | MED (mm) |
|---|---|---|
| SiamRPN++ | 71.52 (↓ 8.79) | 10.6 ± 10.3 (↑ 2.3) |
| Deeds | 74.82 (↓ 10.7) | 9.8 ± 8.9 (↑ 2.4) |
| DLT-SSL | 78.38 (↓ 3.14) | 10.0 ± 11.4 (↑ 1.2) |
| DLT | 83.18 (↓ 3.70) | 8.1 ± 8.7 (↑ 1.2) |
| DLT-Mix | 86.88 (↓ 1.87) | 8.0 ± 10.5 (↑ 0.9) |

In various embodiments of the present disclosure, for parameter analysis, Tables 3-4 present the parameter analysis for different model configurations, with model j representing the final configuration without the multiplication fusion of equation (3) or the center augmentation. It should be noted that the model selection may be based on the validation. Model a may be similar to the final model, except that the global kernel has been disabled, resulting in significant MED increases and demonstrating the importance of the global kernel. Models b and c may explore different global kernel sizes, indicating performance can vary to a certain extent, but may not be overly sensitive to the choice (e.g., kernel). However, excessively large kernel may result in an order of magnitude greater runtime, justifying the choice of a (7, 11, 11) kernel. As model e demonstrates, when the ASE heat map of equation (2) covers excessively large area, it may lose its specificity, resulting in performance degradation. Models f and g may show the effect of different embedding feature dimensions, showing that the performance is not overly sensitive to the choice, as long as the embedding dimension is sufficiently large. In terms of the need for the anatomy signal of ASE, model h may demonstrate its removal considerably increases the MED. Finally, the performance of the model i may demonstrate that the learnable decomposition of equation (6) is critical for accurate tracking. Adding equation (3) and center augmentation to model j may result in the final DLT configuration featured in Table 1.

TABLE 3

Parameter analysis of the components in the DLT.

| id | Equation 6: size | $K_g$ learn | $\psi$, $\varphi$ dimension | Equation 2: G size (n) | Test MED (mm) | Speed (spv) |
|---|---|---|---|---|---|---|
| a | N/A | N/A | 64 | 4 | 9.3 | 1.44 |
| b | 7, 7, 7 | ✓ | 64 | 4 | 9.4 | 2.38 |
| c | 7, 15, 15 | ✓ | 64 | 4 | 7.7 | 24.1 |
| d | 7, 11, 11 | ✓ | 64 | 2 | 7.4 | 3.51 |

TABLE 3-continued

Parameter analysis of the components in the DLT.

| id | Equation 6: $K_g$ size | $\psi, \varphi$ learn | dimension | Equation 2: G size (n) | Test MED (mm) | Speed (spv) |
|---|---|---|---|---|---|---|
| e | 7, 11, 11 | ✓ | 64 | 8 | 8.5 | 3.51 |
| f | 7, 11, 11 | ✓ | 32 | 4 | 8.7 | 2.25 |
| g | 7, 11, 11 | ✓ | 128 | 4 | 7.9 | 5.83 |
| h | 7, 11, 11 | ✓ | 64 | N/A | 9.3 | 3.51 |
| i | 7, 11, 11 | X | 64 | 4 | 9.3 | 3.51 |
| j | 7, 11, 11 | ✓ | 64 | 4 | 7.9 | 3.51 |

TABLE 5

Impact on automatic lesion size measurement when using the OneClick model.

| Input generator | MAE (mm) | Growth accuracy (%) | Response accuracy (%) |
|---|---|---|---|
| DEEDS | 2.69 ± 4.12 | 78.02 | 84.17 |
| DLT | 2.47 ± 3.58 | 79.69 | 85.10 |
| Manual inputs | 2.31 ± 3.16 | 79.69 | 85.56 |

In various embodiments of the present disclosure, for external evaluation, a board-certified radiologist may be

TABLE 4

Parameter analysis and ablation study of the components in the DLT.

| Model id | Ablation study | Equation 6: $K_g$ size | $\psi, \varphi$ learn | dim. | Equation 3 fusion | Equation 2: G size | $\Delta\mu_t$ | Valid MED (mm) | Test MED (mm) | Speed spv |
|---|---|---|---|---|---|---|---|---|---|---|
| a | w/o $K_g$ | NA | NA | 64 | multiply | 4r | X | 8.77 ± 9.88 (↑1.69) | 9.29 ± 10.2 | 1.44 |
| b | smaller $K_g$ | 7, 7, 7 | ✓ | 64 | multiply | 4r | X | 8.26 ± 9.40 (↑1.18) | 9.41 ± 10.2 | 2.38 |
| c | greater $K_g$ | 7, 15, 15 | ✓ | 64 | multiply | 4r | X | 7.24 ± 5.64 (↑0.16) | 7.67 ± 8.78 | 24.1 |
| d | smaller $G_t, G_s$ | 7, 11, 11 | ✓ | 64 | multiply | 2r | X | 7.56 ± 8.95 (↑0.48) | 7.51 ± 8.39 | 3.51 |
| e | greater $G_t, G_s$ | 7, 11, 11 | ✓ | 64 | multiply | 8r | X | 8.40 ± 9.23 (↑1.32) | 8.81 ± 9.80 | 3.51 |
| f | smaller feat. dim. | 7, 11, 11 | ✓ | 32 | multiply | 4r | X | 7.23 ± 6.17 (↑0.15) | 8.72 ± 16.6 | 2.25 |
| g | greater feat. dim. | 7, 11, 11 | ✓ | 128 | multiply | 4r | X | 7.15 ± 6.99 (↑0.07) | 7.91 ± 9.29 | 5.83 |
| h | w/o ASE | 7, 11, 11 | ✓ | 64 | NA | NA | NA | 8.23 ± 9.44 (↑1.15) | 9.34 ± 10.0 | 3.51 |
| i | w/o learn $K_g$ | 7, 11, 11 | X | 64 | multiply | 4r | X | 7.61 ± 9.02 (↑0.53) | 7.98 ± 9.26 | 3.51 |
| j | comparison baseline | 7, 11, 11 | ✓ | 64 | multiply | 4r | X | 7.08 ± 5.25 (↑0.00) | 7.95 ± 8.96 | 3.51 |
|  | Equation 3 with concat. | 7, 11, 11 | ✓ | 64 | concat. | 4r | ✓ | 6.85 ± 9.47 (↓0.23) | 7.94 ± 9.22 | 5.91 |
|  | final configuration | 7, 11, 11 | ✓ | 64 | multiply | 4r | ✓ | 6.69 ± 5.62 (↓0.39) | 6.98 ± 8.95 | 3.51 |

In various embodiments of the present disclosure, trackers may be compared with downstream size measurements. A pre-trained model OneClick, which may take the image $I_s$ and the predicted lesion center $\mu_p$ as its inputs and regress the RECIST diameters of the target lesion, may be used; and only long diameters may be compared for simplicity. Evaluation metrics including mean absolute error (MAE) in mm, growth accuracy, and treatment response accuracy may be used. With the template diameter $d_t$, search diameter $d_s$, and OneClick predicted diameter $d_p$, $d_p$ may be defined as a correct growth prediction if and only if the inequality $(d_s-d_t)(d_p-d_t)>0$ holds. The growth accuracy may represent the percentage of correct growth predictions. The treatment response $\rho=(d_s-d_t)/d_t$ may be defined based on the RECIST guideline, which classifies a treatment response as a partial response if $\rho \leq -0.3$, as progressive disease if $\rho \geq 0.2$, or as stable disease if $\rho \in (-0.3, 0.2)$. Then, the treatment response may be predicted using $\rho_p=(d_p-d_t)/d_t$.

In various embodiments of the present disclosure, the DLT, DEEDS, and manual inputs, for example, the ground truth lesion centers, may be tested. Table 5 illustrates the impact on automatic lesion size measurement when using the OneClick model. The DLT may outperform DEEDS in MAE by 0.22 mm, which is an 8% improvement. Compared with manual inputs, the DLT may exhibit the same growth accuracy and be only 0.46% lower in the treatment response accuracy.

further invited to manually assess the DLT with 100 longitudinal studies recruited from real-life clinical workflows. In total, there are 536 lesions need to be monitored; and the tracking results of the DLT may be compared with DEEDS in Table 6. The DLT may deliver about 88.4% CPM accuracy and outperform DEEDS by about 2.8%. Furthermore, the DLT may require only about 4.7 seconds to process a whole body CT, which is over 14 times faster than DEEDS; and the results may also underscore the value of the DLS dataset.

TABLE 6

External evaluation on the DLT and DEEDS.

| Method | CPM@Radius | speed (spv) |
|---|---|---|
| DEEDS | 85.6 | 67.1 ± 17.8 |
| DLT | 88.4 | 4.7 ± 0.35 |

In various embodiments of the present disclosure, the dataset with 3891 lesion pairs, collected from DeepLesion, may be constructed to train and evaluate different tracking solutions (approaches). Although more training pairs can promote a stronger tracker, labor and time costs preclude easily collecting and annotating a large number of longitudinal studies for a specific clinical application, such that the effective SSL strategy may be used to train trackers. Importantly, such strategy may train lesion trackers using images from only one time point, meaning non-longitudinal datasets which are more readily collected may be used, which allows for a more ready introduction of more lesion instances with varied appearances and sizes. With the DLT and model training strategies, about 89% matching accuracy may be achieved on the test set of 480 lesion pairs. Meanwhile, the DLT may be robust to inaccurate tracking initializations, for example, the given initial lesion center. In robustness study of the present disclosure, inaccurate initialization may cause about 10% accuracy drops on SiamRPN++ and DEEDS. In contrast, the accuracy of the DLT may only decrease by about 1.9%. The DLT may be then applied to the external testing set of 100 real-life clinical longitudinal studies, delivering about 88% matching accuracy and demonstrating desirable generalizability. Finally, the DLT may be plugged into the lesion monitoring pipeline to simulate automatic treatment monitoring. The workflow may assess lesion treatment responses with about 85% accuracy, which is only about 0.46% lower than the accuracy of manual inputs.

According to various embodiments of the present disclosure, the DLT may be introduced as the new public benchmark for lesion tracking. Due to the different setup of medical applications, the DLT may differ from general visual trackers in two aspects. First, the DLT may not regress bounding boxes for target lesions because, as mentioned before in the present disclosure, the lesion size may be accurately predicted by the downstream measurement module. Second, the DLT may not perform long-term tracking because time points in longitudinal studies may be much less than general videos. Furthermore, manual calibration may occur more frequently in lesion tracking than general object tracking. The DLT has been demonstrated effective for lesion tracking, outperforming the comprehensive set of baselines that represent various tracking strategies. The DLT may be trained via either supervised or self-supervised learning, where the combination of both training schemes may result in desirable performance and robustness.

The present disclosure also provides a deep lesion tracker device. The device includes a memory, containing a computer program stored thereon; and a processor, coupled with the memory and configured, when the computer program being executed, to perform a method including: providing an image pair including a search image and a template image; inputting the search image into a first three-dimensional DenseFPN (feature pyramid network) of an image encoder, and inputting the template image into a second three-dimensional DenseFPN of the image encoder to extract image features of the search image and the template image in three different scales, where the first and second three-dimensional DenseFPNs are configured with shared weights; encoding anatomy signals of the search image and the template image as Gaussian heatmaps centered at lesion locations, inputting the Gaussian heatmap of the template image into a first anatomy signal encoders (ASE), and inputting the Gaussian heatmap of the search image into a second ASE to extract anatomy features of the search image and the template image in three different scales, where the first and the second ASEs are configured with shared weights; inputting the image features and the anatomy features into a fast cross-correlation layer to generate correspondence maps, and computing a probability map according to the correspondence maps; and performing supervised learning or self-supervised learning to predict a lesion center in the search image.

The present disclosure also provides a computer program product comprising a non-transitory computer-readable storage medium and program instructions stored therein, the program instructions being configured to be executable by a computer to cause the computer to implement operations comprising: providing an image pair including a search image and a template image; inputting the search image into a first three-dimensional DenseFPN (feature pyramid network) of an image encoder, and inputting the template image into a second three-dimensional DenseFPN of the image encoder to extract image features of the search image and the template image in three different scales, where the first and second three-dimensional DenseFPNs are configured with shared weights; encoding anatomy signals of the search image and the template image as Gaussian heatmaps centered at lesion locations, inputting the Gaussian heatmap of the template image into a first anatomy signal encoders (ASE), and inputting the Gaussian heatmap of the search image into a second ASE to extract anatomy features of the search image and the template image in three different scales, where the first and the second ASEs are configured with shared weights; inputting the image features and the anatomy features into a fast cross-correlation layer to generate correspondence maps, and computing a probability map according to the correspondence maps; and performing supervised learning or self-supervised learning to predict a lesion center in the search image.

While the disclosure has been illustrated with respect to one or more implementations, alterations and/or modifications can be made to the illustrated examples without departing from the spirit and scope of the appended claims. In addition, while a particular feature of the disclosure may have been disclosed with respect to only one of several implementations, such feature may be combined with one or more other features of the other implementations as may be desired and advantageous for any given or particular function. Furthermore, to the extent that the terms "including", "includes", "having", "has", "with", or variants thereof are used in either the detailed description and the claims, such terms are intended to be inclusive in a manner similar to the term "comprising." The term "at least one of" is used to mean one or more of the listed items can be selected.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. In certain cases, the numerical values as stated for the parameter can take on negative values.

Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A deep lesion tracker method for medical images, the method comprising:
   providing an image pair including a search image and a template image;
   inputting the search image into a first three-dimensional DenseFPN (feature pyramid network) of an image encoder, and inputting the template image into a second three-dimensional DenseFPN of the image encoder to extract image features of the search image and the template image in three different scales, wherein the first and second three-dimensional DenseFPNs are configured with shared weights;

encoding anatomy signals of the search image and the template image as Gaussian heatmaps centered at lesion locations, inputting the Gaussian heatmap of the template image into a first anatomy signal encoders (ASE) and inputting the Gaussian heatmap of the search image into a second ASE to extract anatomy features of the search image and the template image in three different scales, wherein the first and the second ASEs are configured with shared weights;

inputting the image features and the anatomy features into a fast cross-correlation layer to generate correspondence maps, and computing a probability map according to the correspondence maps; and performing supervised learning or self-supervised learning to predict a lesion center in the search image.

2. The method according to claim 1, wherein encoding the anatomy signals as the Gaussian heatmaps includes:

for the template image, using a location and a size of a template lesion to compute the anatomy signals of the template image; and for the search image, using an affine-projected location and an affine-projected size of the template lesion to compute the anatomy signals of the search image.

3. The method according to claim 2, wherein inputting the image features and the anatomy features into the fast cross-correlation layer to generate the correspondence maps includes:

fusing the image features of the template image and the anatomy features of the template image.

4. The method according to claim 3, wherein after fusing the image features of the template image and the anatomy features of the template image, the method further includes:

defining a cropping function to extract a template kernel K and another template kernel $K_g$, wherein:

a size of the template kernel $K_g$ is greater than a size of the template kernel K; and the template kernel $K_g$ is decomposed into kernels $K_{g,x}$, $K_{g,y}$, and $K_{g,z}$, along axial, coronal, and sagittal directions, respectively.

5. The method according to claim 4, wherein a correspondence map is computed by:

$$M = (K * S) + \left( \sum_{i \in x, y, z} K_{g,i} * S \right)$$

wherein + denotes element-wise sum, * denotes multiplication, $S = \psi(I_s) \odot \phi(G_s)$, $I_s$ is the search image, $G_s$ is an anatomy signal map of the search image, $\odot$ denotes element-wise multiplication, $\psi$ and $\phi$ denote network encoders that generate image features and anatomy features, respectively.

6. The method according to claim 5, wherein after computing the correspondence map, the method further includes:

determining the lesion center in the search image according to the probability map computed based on the correspondence maps.

7. A deep lesion tracker device for medical images comprising:

a memory, containing a computer program stored thereon; and a processor, coupled with the memory and configured, when the computer program being executed, to perform a method including:

providing an image pair including a search image and a template image;

inputting the search image into a first three-dimensional DenseFPN (feature pyramid network) of an image encoder and inputting the template image into a second three-dimensional DenseFPN of the image encoder to extract image features of the search image and the template image in three different scales, wherein the first and second three-dimensional DenseFPNs are configured with shared weights;

encoding anatomy signals of the search image and the template image as Gaussian heatmaps centered at lesion locations, and inputting the Gaussian heatmap of the template image into a first anatomy signal encoders (ASE) and inputting the Gaussian heatmap of the search image into a second ASE to extract anatomy features of the search image and the template image in three different scales, wherein the first and the second ASEs are configured with shared weights;

inputting the image features and the anatomy features into a fast cross-correlation layer to generate correspondence maps, and computing a probability map according to the correspondence maps; and performing supervised learning or self-supervised learning to predict a lesion center in the search image.

8. The device according to claim 7, wherein encoding the anatomy signals as the Gaussian heatmaps includes:

for the template image, using a location and a size of a template lesion to compute the anatomy signals of the template image; and for the search image, using an affine-projected location and an affine-projected size of the template lesion to compute the anatomy signals of the search image.

9. The device according to claim 8, wherein inputting the image features and the anatomy features into the fast cross-correlation layer to generate the correspondence maps includes:

fusing the image features of the template image and the anatomy features of the template image.

10. The device according to claim 9, wherein after fusing the image features of the template image and the anatomy features of the template image, the method further includes:

defining a cropping function to extract a template kernel K and another template kernel $K_g$, wherein:

a size of the template kernel $K_g$ is greater than a size of the template kernel K; and the template kernel $K_g$ is decomposed into kernels $K_{g,x}$, $K_{g,y}$, and $K_{g,z}$, along axial, coronal, and sagittal directions, respectively.

11. The device according to claim 10, wherein a correspondence map is computed by:

$$M = (K * S) + \left( \sum_{i \in x, y, z} K_{g,i} * S \right)$$

wherein + denotes element-wise sum, * denotes multiplication, $S = \psi(I_s) \odot \phi(G_s)$, $I_s$ is the search image, $G_s$ is an anatomy signal map of the search image, $\odot$ denotes element-wise multiplication, and $\psi$ and $\phi$ denote network extractors that generate image features and anatomy features, respectively.

12. The device according to claim 11, after computing the correspondence map, the method further includes:

determining the lesion center in the search image according to the probability map computed based on the correspondence maps.

13. A computer program product comprising a non-transitory computer-readable storage medium and program instructions stored therein, the program instructions being configured to be executable by a computer to cause the computer to implement a method comprising:

providing an image pair including a search image and a template image;

inputting the search image into a first three-dimensional DenseFPN (feature pyramid network) of an image encoder and inputting the template image into a second three-dimensional DenseFPN of the image encoder to extract image features of the search image and the template image in three different scales, wherein the first and second three-dimensional DenseFPNs are configured with shared weights;

encoding anatomy signals of the search image and the template image as Gaussian heatmaps centered at lesion locations, and inputting the Gaussian heatmap of the template image into a first anatomy signal encoders (ASE) and inputting the Gaussian heatmap of the search image into a second ASE to extract anatomy features of the search image and the template image in three different scales, wherein the first and the second ASEs are configured with shared weights;

inputting the image features and the anatomy features into a fast cross-correlation layer to generate correspondence maps, and computing a probability map according to the correspondence maps; and performing supervised learning or self-supervised learning to predict a lesion center in the search image.

14. The computer program product according to claim 13, wherein encoding the anatomy signals as the Gaussian heatmaps includes:

for the template image, using a location and a size of a template lesion to compute the anatomy signals of the template image; and for the search image, using an affine-projected location and an affine-projected size of the template lesion to compute the anatomy signals of the search image.

15. The computer program product according to claim 14, wherein inputting the image features and the anatomy features into the fast cross-correlation layer to generate the correspondence maps includes:

fusing the image features of the template image and the anatomy features of the template image.

16. The computer program product according to claim 15, wherein after fusing the image features of the template image and the anatomy features of the template image, the method further includes:

defining a cropping function to extract a template kernel K and another template kernel $K_g$, wherein:

a size of the template kernel $K_g$ is greater than a size of the template kernel K; and the template kernel $K_g$ is decomposed into kernels $K_{g,x}$, $K_{g,y}$ and $K_{g,z}$, along axial, coronal, and sagittal directions, respectively.

17. The computer program product according to claim 16, wherein a correspondence map is computed by:

$$M = (K*S) + \left(\sum_{i \in x,y,z} K_{g,i} * S\right)$$

wherein + denotes element-wise sum, * denotes multiplication, $S=\psi(I_s) \odot \phi(G_s)$, $I_s$ is the search image, $G_s$ is an anatomy signal map of the search image, $\odot$ denotes element-wise multiplication, and $\psi$ and $\phi$ denote network encoders that generate image features and anatomy features, respectively.

18. The computer program product according to claim 17, wherein after computing the correspondence map, the method further includes:

determining the lesion center in the search image according to the probability map computed based on the correspondence maps.

* * * * *